(12) United States Patent
Funakoshi et al.

(10) Patent No.: US 7,928,143 B2
(45) Date of Patent: Apr. 19, 2011

(54) METHOD FOR PREVENTING AND/OR TREATING NEURODEGENERATIVE DISEASES

(75) Inventors: Yosuke Funakoshi, Osaka (JP); Ken Mizushima, Osaka (JP); Toshio Takakuwa, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 1245 days.

(21) Appl. No.: 10/574,489

(22) PCT Filed: Oct. 1, 2004

(86) PCT No.: PCT/JP2004/014893
§ 371 (c)(1),
(2), (4) Date: Jul. 25, 2006

(87) PCT Pub. No.: WO2005/032537
PCT Pub. Date: Apr. 14, 2005

(65) Prior Publication Data
US 2007/0043116 A1    Feb. 22, 2007

Related U.S. Application Data

(60) Provisional application No. 60/507,952, filed on Oct. 3, 2003.

(30) Foreign Application Priority Data

Jun. 11, 2004    (JP) ................................. 2004-174577

(51) Int. Cl.
*A61K 31/20* (2006.01)
*A01N 37/00* (2006.01)
*C07C 57/00* (2006.01)
*C07C 59/00* (2006.01)
*C07C 53/00* (2006.01)
*C08G 63/48* (2006.01)

(52) U.S. Cl. .......................................... 514/558; 554/1
(58) Field of Classification Search .................. 514/558; 554/1
See application file for complete search history.

(56) References Cited

U.S. PATENT DOCUMENTS 5,693,636 A * 12/1997 Bondinell et al. ............ 514/221
6,608,221 B1 * 8/2003 Toda et al. ........................ 554/1

FOREIGN PATENT DOCUMENTS

| EP | 0 632 008 A1 | 1/1995 |
| EP | 1 174 131 A1 | 1/2002 |
| WO | WO 03/007992 A1 | 1/2003 |

OTHER PUBLICATIONS

Weinreb, R. N. "Glaucoma neuroprotection: What is it? Why is it needed?" Can J Ophthalmol, 2007, vol. 42, No. 3, pp. 396-398.*
Tateishi et al."Astrocytic Activation and Delayed Infarct Expansion After Permanent Focal Ischemia in Rats. Part II: Suppression of Astrocytic Activation by a Novel Agent (R)-(−)-2-propyloctanoic acid (ONO-2506) Leads to Mitigation of Delayed Infarct Expansion . . .",Journal of Cerebral Blood Flow & Metabolism, Jun. 2002, vol. 22, No. 6, pp. 723-734.*
Honjo K et. al. "Effects of ONO-2506 Combined With Thrombolytic Therapy in a Rat Model of Thrombotic Focal Cerebral Ischemia" vol. 27, No. 2. Nov. 10, 2001, p. 2301.
Asano T. et. al : "Arundic Acid (ONO-2506) Ameliorates Delayed Ischemic Brain Damage Be Preventing Astrocytic Overproduction of S100B" Current Drug Targets. CNS & Neurological Disorders, Bentham Science Publishers, Hilversum, NL, vol. 4, No. 2, Apr. 1, 2005, p. 127-142.
For the Arundic Acid (ONO-2506) Stroke Study Group et. al. "Safety and Tolerability of Arundic Acid in Acute Ischemic Stroke" Journal of Neurological Sciences, Elsevier Scientific Publishing Co, Amsterdam, NL, vol. 251, No. 1-2, Dec. 21, 2006, pp. 50-56.
European Supplementary Search Report issued in application No. 04773691.3-2123 dated Jan. 12, 2010.

* cited by examiner

*Primary Examiner* — Sreeni Padmanabhan
*Assistant Examiner* — Kendra D Carter
(74) *Attorney, Agent, or Firm* — Sughrue Mion, PLLC

(57) ABSTRACT

The invention relates to a neurodegenerative disease treating agent for parenteral use, which comprises (2R)-2-propyloctanoic acid or a salt thereof.
Since the neurodegenerative disease treating agent of the present invention comprising (2R)-2-propyloctanoic acid or a salt thereof, characterized in that a dosage exceeding about 100 mg per dose is parenterally administered, shows neuropathy improving effect and S-100β increase inhibiting effect in patients with cerebral infarction, it is useful for the treatment of neurodegenerative diseases including cerebral infarction. In addition, it is also useful as a neural regeneration agent after transplantation.

14 Claims, 2 Drawing Sheets

METHOD FOR PREVENTING AND/OR TREATING NEURODEGENERATIVE DISEASES

CROSS-REFERENCE TO RELATED APPLICATIONS

This is an application filed pursuant to 35 U.S.C. Section 111 (a) with claiming the benefit of U.S. provisional application Ser. No. 60/507,952 filed Oct. 3, 2003 under the provision of 35 U.S.C. 111(b), pursuant to 35 U.S.C. Section 119(e) (1).

TECHNICAL FIELD

The present invention relates to a medicament comprising (2R)-2-propyloctanoic acid or a salt thereof, which is parenterally administered for the prevention and/or treatment of a neurodegenerative disease, for the prevention and/or treatment of a neuropathy or for the prevention and/or treatment of a disease whose treatment requires neural regeneration. Particularly, it relates to a method for preventing and/or treating cerebral infarction, which comprises parenterally administering (2R)-2-propyloctanoic acid or a salt thereof at a high dose of exceeding about 100 mg per one administration.

BACKGROUND ART

Cerebral infarction is a disease exemplified as a cause of stroke together with cerebral bleeding and subarachnoid hemorrhage. Cerebral infarction is a neurodegenerative disease in which arteriosclerosis of a brain blood vessel or obstruction of a brain blood vessel caused by thrombi brought therein stops blood flow ahead thereof to cease feeding of nutrients into brain cells and finally causes the death of nerve cells. In addition, even when a patient with cerebral infarction has escaped sudden death, it sometimes leaves serious secondary diseases such as hemiplegia and aphasia caused by functional disorder of nerve cells. In the treatment of cerebral infarction, it is considered in general that, after obstruction of the brain blood flow, blood flow must be restored before brain tissues cause irreversible changes and result in necrosis. On the other hand, it is considered that there is a therapeutic time window (hereinafter referred to as "TTW") in cerebral infarction, within which cerebral infarction can be treated almost without leaving secondary diseases. Although the length of TTW is considered to differ in each case of the disease depending on the developing degree of collateral circulation, but is roughly 3 hours, or about 6 hours at the longest, after the stroke.

Examples of the currently and mainly used as cerebral infarction treating agents include thrombolytic agents such as tissue plasminogen activator (t-PA) and urokinase, anticoagulants such as warfarin and heparin, and free radical scavengers such as Radicut (edalabon) (product name: manufactured by Mitsubishi Pharma Corporation). However, t-PA shows its efficacy only when it is administered within 3 hours after onset of cerebral infarction, namely within TTW, and with respect to anticoagulants, since it takes several days to express the anticoagulation action, the effects could hardly be said to be sufficient. In addition, since Radicut (product name: manufactured by Mitsubishi Pharma Corporation) sometimes causes serious side effects such as nephropathy, its use requires sufficient precautions. Thus, since the currently used cerebral infarction treating agents have problems in terms of their effect or toxicity and also have many limitations regarding their use, the development of useful therapeutic agents has been desired earnestly.

Also, involvement of S-100 protein in various neurodegenerative diseases has been revealed in recent years. For example, it has been reported that measurement results of blood S-100 protein can be used in the diagnosis of cerebral lesions and neurological damages in stroke (Stroke, vol. 28, pp. 1956-1960 (1997)). It is known that S-100$\beta$, a kind of the S-100$\beta$ protein, is a protein which is present at a high concentration in glial cells and Schwann cells in the central nervous system and peripheral nervous system and also in anterior pituitary cells and Langerhans cells. It is known that S-100$\beta$ in cerebrospinal fluid or blood is increased by cerebral infarction, subarachnoid hemorrhage, head injury, various neurodegenerative diseases or a nervous complication after a heart-lung bypass operation.

On the other hand, it has been reported that (2R)-2-propyloctanoic acid, which has activity of reducing the intracellular S-100$\beta$ content, has a potentiality to be used as an agent for the treatment or prevention of various cranial nerve diseases including stroke, through the improvement of the function of abnormally activated astrocyte (e.g., see Tateishi, N. and 8 others, Journal of Cerebral Blood Flow & Metabolism, 22(6), 723-734 (2002)).

Also, since pentanoic acid derivatives including (2R)-2-propyloctanoic acid have an action to improve functions of astrocyte, it is known that they are effective for treating stroke and other various diseases. In addition, it has been described that they are orally administered once to several times a day within a range of 1 to 1,000 mg per one dose per adult, or parenterally administered once to several times a day within a range of 0.1 to 100 mg per one dose (e.g., see the specification of European Patent No. 0632008).

Further, a method for treating a cerebral ischemic disease which comprises administering (2R)-2-propyloctanoic acid or a salt thereof in combination with thrombolytic agents such as a tissue plasminogen activator is known (e.g., see the specification of International Publication No. 03/007992).

However, the therapeutic method described in said patent documents are methods which are limited to parenteral administration of at most 100 mg of the compound per one administration. Particularly, it is not known that the compound can show its efficacy safely in patients by its parenteral administration at a dose of exceeding 100 mg per one administration.

DISCLOSURE OF THE INVENTION

In general, when a medicament is administered at a high dose, or even at a low dose but for a prolonged period of time, side effects and the like are expressed in many cases, bringing about limitations in the treatment of intended patients and thus resulting in insufficient therapeutic effects. Particularly, no reports have so far been made on the clinically sufficiently satisfactory medicaments as therapeutic methods for neurodegenerative diseases, for cerebral infarction in particular. For example, since a free radical scavenger, radicut, has serious side effects such as acute renal insufficiency, it is necessary to carry out renal function tests during and after its administration.

As a result of intensive studies in order to find a therapeutic agent for a neurodegenerative disease, particularly cerebral infarction, the present inventors have found that administration of high-dose (2R)-2-propyloctanoic acid or a salt thereof of exceeding 100 mg per dose, which is an unconventionally high dose, is sufficiently useful on a clinical ground in obtaining markedly excellent effects of treating cerebral infarction, such as effects of improving neuropathy and inhibiting S-100β increase, extremely safely and causing almost no side effects, and based on this finding, the present inventors have made further studies in greater detail and accomplished the present invention.

More specifically, the present invention relates to

[1] a method for preventing and/or treating a neurodegenerative disease, neuropathy or a disease whose treatment requires neural regeneration, which comprises parenteral administration of an effective amount of (2R)-2-propyloctanoic acid or a salt thereof to a mammal;

[2] the method according to above [1], wherein the disease to be treated with the method is neurodegenerative disease;

[3] the method according to above [1], wherein the amount per dose in the parenteral administration is within a range of about 100 mg to about 2,000 mg;

[4] the method according to above [2], wherein the neurodegenerative disease is stroke;

[5] the method according to above [2], wherein the neurodegenerative disease is cerebral infarction;

[6] the method according to above [1], wherein the parenteral administration is intravenous administration;

[7] the method according to above [6], wherein the intravenous administration is continuous administration;

[8] the method according to above [7], wherein the continuous administration is infusion bag administration;

[9] the method according to above [1], wherein the dose of parenteral administration per once a day during an administration period of 1 day to 100 days is within a range of about 100 mg to about 2,000 mg;

[10] the method according to above [9], wherein the administration period is from 1 day to 10 days;

[11] the method according to above [10], wherein the administration period is 3 days, 4 days, 5 days, 6 days or 7 days;

[12] the method according to above [11], wherein the administration period is 7 days;

[13] the method according to above [1], wherein the dose per 1 kg of body weight of a patient is within a range of about 2 mg to about 12 mg;

[14] the method according to above [13], wherein the dose per 1 kg of body weight of a patient is about 2 mg, about 4 mg, about 6 mg, about 8 mg, about 10 mg or about 12 mg;

[15] the method according to above [14], wherein the dose per 1 kg of body weight of a patient is about 4 mg or about 8 mg;

[16] the method according to above [1], which is a method for inhibition of S-100β increase;

[17] a method for inhibition of S-100β increase, which comprises parenterally administering to a mammal an effective amount of (2R)-2-propyloctanoic acid or a salt thereof;

[18] the method according to above [17], wherein the amount per dose in the parenteral administration is within a range of about 100 mg to about 2,000 mg;

[19] the method according to above [17], wherein the parenteral administration is intravenous administration;

[20] the method according to above [17], wherein the dose of parenteral administration per once a day during an administration period of 1 day to 100 days is within a range of about 100 mg to about 2,000 mg;

[21] the method according to above [17], wherein the dose per 1 kg of body weight of a patient is within a range of about 2 mg to about 12 mg;

[22] a parenterally administered agent for preventing and/or treating a neurodegenerative disease, a neuropathy or a disease whose treatment requires neural regeneration, which comprises (2R)-2-propyloctanoic acid or a salt thereof;

[23] use of (2R)-2-propyloctanoic acid or a salt thereof for the manufacture of a parenterally administered agent for preventing and/or treating a neurodegenerative disease, a neuropathy or a disease whose treatment requires neural regeneration;

[24] a method for preventing and/or treating cerebral infarction, which comprises parenterally administering to a mammal an effective amount of (2R)-2-propyloctanoic acid or a salt thereof in combination with an effective amount of a tissue plasminogen activator;

[25] the method according to above [24], wherein the dose of (2R)-2-propyloctanoic acid or a salt thereof per 1 kg of body weight of a patient is about 4 mg or about 8 mg, and the dose of the tissue plasminogen activator per 1 kg of body weight of a patient is about 0.6 mg or about 0.9 mg;

[26] the method according to above [25], wherein the administration is started within 3 hours after onset of the cerebral infarction;

[27] a parenterally administered agent for preventing and/or treating cerebral infarction, which comprises (2R)-2-propyloctanoic acid or a salt thereof in combination with a tissue plasminogen activator;

[28] use of (2R)-2-propyloctanoic acid or a salt thereof in combination with a tissue plasminogen activator for the manufacture of a parenterally administered agent for preventing and/or treating cerebral infarction;

[29] the method according to above [1], [17] or [24], wherein (2R)-2-propyloctanoic acid is used;

[30] the agent according to above [22] or [27], wherein (2R)-2-propyloctanoic acid is comprised;

[31] the use according to above [23] or [28], wherein (2R)-2-propyloctanoic acid is used;

[32] a method for treating cerebral infarction, which comprises continuous administration of (2R)-2-propyloctanoic acid intravenously using infusion bag at a dose of about 4 mg or about 8 mg per 1 kg of body weight of a patient during administration period for 7 days;

[33] an agent for treating cerebral infarction, which comprises continuous administration of (2R)-2-propyloctanoic acid intravenously using infusion bag at a dose of about 4 mg or about 8 mg per 1 kg of body weight of a patient during administration period for 7 days;

[34] use of (2R)-2-propyloctanoic acid for the manufacture of an agent for treating cerebral infarction, which comprises continuous administration of (2R)-2-propyloctanoic acid intravenously using infusion bag at a dose of about 4 mg or about 8 mg per 1 kg of body weight during administration period for 7 days;

[35] an agent for inhibition of S-100β increase, which comprises (2R)-2-propyloctanoic acid or a salt thereof;

[36] the agent according to above [35], wherein (2R)-2-propyloctanoic acid is comprised;

[37] use of (2R)-2-propyloctanoic acid or a salt thereof for the manufacture of an agent for inhibition of S-100β increase, which comprises (2R)-2-propyloctanoic acid or a salt thereof;

[38] the use according to above [37], wherein (2R)-2-propyloctanoic acid is used;

[39] the parenterally administered agent according to above [22], wherein the disease to be treated with the agent is neurodegenerative disease;

[40] the parenterally administered agent according to above [22], which is parenterally administered in an amount per dose of about 100 mg to about 2,000 mg;

[41] the parenterally administered agent according to above [39], wherein the neurodegenerative disease to be treated is stroke;

[42] the parenterally administered agent according to above [39], wherein the neurodegenerative disease to be treated with the agent is cerebral infarction;

[43] the parenterally administered agent according to above [22], which is parenterally administered by intravenous administration;

[44] the parenterally administered agent according to above [43], wherein the intravenous administration is continuous administration;

[45] the parenterally administered agent according to above [44], wherein the continuous administration is infusion bag administration;

[46] the parenterally administered agent according to above [22], which is parenterally administered once a day during an administration period of 1 day to 100 days in an amount of about 100 mg to about 2,000 mg per dose;

[47] the parenterally administered agent according to above [46], wherein the administration period is from 1 day to 10 days;

[48] the parenterally administered agent according to above [47], wherein the administration period is 3 days, 4 days, 5 days, 6 days or 7 days;

[49] the parenterally administered agent according to above [48], wherein the administration period is 7 days;

[50] the parenterally administered agent according to above [22], which is administered in an amount of about 2 mg to about 12 mg per 1 kg of body weight of a patient;

[51] the parenterally administered agent according to above [50], wherein the dose per 1 kg of body weight of a patient is about 2 mg, about 4 mg, about 6 mg, about 8 mg, about 10 mg or about 12 mg;

[52] the parenterally administered agent according to above [51], wherein the dose per 1 kg of body weight of a patient is about 4 mg or about 8 mg;

[53] the parenterally administered agent according to above [22], which is administered for inhibition of S-100β increase; [54] the agent for inhibition of S-100β increase according to above [35], which is parenterally administered to a mammal in an effective amount of about 100 mg to about 2,000 mg per dose;

[55] the agent for inhibition of S-100β increase according to above [54], which is parenterally administered by intravenous administration;

[56] the agent for inhibition of S-100β increase according to above [54], which is parenterally administered during an administration period of 1 day to 100 days in an amount of about 100 mg to about 2,000 mg once a day;

[57] the agent for inhibition of S-100β increase according to above [54], which is administered in an amount of about 2 mg to about 12 mg per 1 kg of body weight of a patient;

[58] the parenterally administered agent for preventing and/or treating cerebral infarction according to above [27], which is administered to a mammal in an effective amount, wherein the dose of (2R)-2-propyloctanoic acid or a salt thereof per 1 kg of body weight of a patient is about 4 mg or about 8 mg, and the dose of the tissue plasminogen activator per 1 kg of body weight of a patient is about 0.6 mg or about 0.9 mg;

[59] the parenterally administered agent for preventing and/or treating cerebral infarction method according to above [58], which is administered within 3 hours after onset of the cerebral infarction;

[60] the use of (2R)-2-propyloctanoic acid or a salt thereof according to above [23], wherein the disease to be treated is neurodegenerative disease;

[61] the use of (2R)-2-propyloctanoic acid or a salt thereof according to above [23], wherein the amount per dose in the parenteral administration is within a range of about 100 mg to about 2,000 mg;

[62] the use according to above [60], wherein the neurodegenerative disease is stroke;

[63] the use according to above [60], wherein the neurodegenerative disease is cerebral infarction;

[64] the use of (2R)-2-propyloctanoic acid or a salt thereof according to above [23], wherein the parenteral administration is intravenous administration;

[65] the use according to above [64], wherein the intravenous administration is continuous administration;

[66] the use according to above [65], wherein the continuous administration is infusion bag administration;

[67] the use of (2R)-2-propyloctanoic acid or a salt thereof according to above [23], wherein the dose of parenteral administration once a day during an administration period of 1 day to 100 days is within a range of about 100 mg to about 2,000 mg;

[68] the use according to above [67], wherein the administration period is from 1 day to 10 days;

[69] the use according to above [68], wherein the administration period is 3 days, 4 days, 5 days, 6 days or 7 days;

[70] the use according to above [69], wherein the administration period is 7 days;

[71] the use of (2R)-2-propyloctanoic acid or a salt thereof according to above [23], wherein the dose per 1 kg of body weight of a patient is within a range of about 2 mg to about 12 mg;

[72] the use according to above [71], wherein the dose per 1 kg of body weight of a patient is about 2 mg, about 4 mg, about 6 mg, about 8 mg, about 10 mg or about 12 mg;

[73] the use according to above [72], wherein the dose per 1 kg of body weight of a patient is about 4 mg or about 8 mg;

[74] the use of (2R)-2-propyloctanoic acid or a salt thereof according to above [23], which is a use for the purpose of inhibition of S-100β increase;

[75] the use of (2R)-2-propyloctanoic acid or a salt thereof for the manufacture of an agent according to above [37], which comprises parenterally administering to a mammal an effective amount of (2R)-2-propyloctanoic acid or a salt thereof, wherein the amount per dose in the parenteral administration is within a range of about 100 mg to about 2,000 mg;

[76] the use of (2R)-2-propyloctanoic acid or a salt thereof for the manufacture of an agent according to above [37], wherein the parenteral administration is intravenous administration;

[77] the use of (2R)-2-propyloctanoic acid or a salt thereof for the manufacture of an agent according to above [37], wherein the dose of parenteral administration per once a day during an administration period of 1 day to 100 days is within a range of about 100 mg to about 2,000 mg;

[78] the use of (2R)-2-propyloctanoic acid or a salt thereof for the manufacture of an agent according to above [37], wherein the dose per 1 kg of body weight of a patient is within a range of about 2 mg to about 12 mg; and the like.

DETAILED DESCRIPTION OF THE INVENTION

In the present invention, the (2R)-2-propyloctanoic acid is a compound represented by a formula (I)

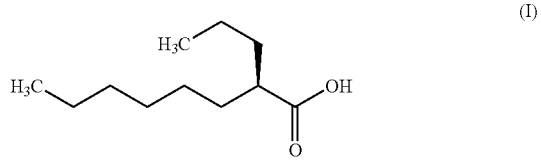

(I)

(wherein the symbol ╱ means β-configuration). As the salt of (2R)-2-propyloctanoic acid, a pharmaceutically acceptable salt is preferable. As the pharmaceutically acceptable salt, those which have no toxicity and are soluble in water are desirable.

Examples of the appropriate salt of (2R)-2-propyloctanoic acid include a salt with an inorganic base, a salt with an organic base, a salt with a basic natural amino acid, and the like. Examples of the salt with inorganic base include alkali metal salts (e.g., sodium salt, potassium salt, lithium salt), ammonium salts (e.g., tetramethylammonium salt, tetrabutylammonium salt) and the like. Examples of the salt with organic base include salts with alkyl amine (e.g., methylamine, dimethylamine, trimethylamine, triethylamine), heterocyclic amine (e.g., pyridine, picoline, piperidine), alkanolamine (e.g., ethanolamine, diethanolamine, triethanolamine), dicyclohexylamine, N,N'-dibenzylethylenediamine, cyclopentylamine, benzylamine, phenetylamine, tris(hydroxymethyl)methylamine, N-methyl-D-glucamine and the like. The salt with basic natural amino acid is not particularly limited, so long as it is a salt with a basic amino acid which is distributed in the natural sources and can be purified, and its preferred examples include salts with arginine, lysine, ornithine, histidine and the like. Among these salts, preferred are an alkali metal salt or a basic natural amino acid salt, and particularly preferred is a sodium salt.

In the present invention, (2R)-2-propyloctanoic acid or a salt thereof is not limited to a substantially pure single substance, and it may contain impurities (e.g., a byproduct, a solvent, a material originated from the production process, a degraded product), within such a range that they are acceptable as pharmaceutical materials. The amount of impurities acceptable as pharmaceutical materials varies depending on each impurity to be contained, and it is desirable for example that heavy metals are about 20 ppm or less, S-forms as optical isomers are about 1.49% by mass or less, 2-propanol and heptane as residual solvents are about 5,000 ppm or less in total and the water content is about 0.2% by mass or less.

In the present invention, (2R)-2-propyloctanoic acid or a salt thereof can be produced in accordance with a known method, for example, a method described in the specification of European Patent No. 0632008, International Publication No. 99/58513, International Publication No. 00/48982, Japanese Patent No. 3032447, Japanese Patent No. 3084345 or the like, or by optionally combining these methods, and, as a pharmaceutical composition for parenteral administration use, it can be prepared into various dosage forms such as ointments, gels, creams, fomentations, adhesive preparations, liniments, atomized agents, inhalations, sprays, eye drops, suppositories, pessaries, injections and the like. Regarding the pharmaceutical composition, it may be in any dosage forms which can be parenterally administered to a patient of a neurodegenerative disease, a patient of a neuropathy or a patient of a disease whose treatment requires neural regeneration, but when both of its immediate effect and blood concentration control are taken into consideration, dosage forms which can be intravenously administered, such as transfusion preparations, injections and the like, are desirable. Preferred as such dosage forms are those which contain 100 mg or more of (2R)-2-propyloctanoic acid or a salt thereof per one administration. As the substances to be used in pharmaceutical compositions such as transfusion preparations and injections, they are optionally selected from additives described, for example, in Dictionary of Pharmaceutical Additives (edited by Japan Pharmaceutical Additives Association), published by Yakuji Nipposha in 2000, such as metal salts (e.g., sodium phosphate, disodium hydrogenphosphate, sodium carbonate, sodium sulfite) and pH adjuster (e.g., sodium hydroxide), as well as a stabilizing agent, a surfactant, a buffer agent, a solubilizing agent, an antioxidant, an antifoaming agent, a tonicity agent, an emulsifying agent, a suspending agent, a preservative, a soothing agent, a resolvent, a solubilization assisting agent and the like, which are generally used in injections, and also from components generally used in transfusions such as electrolytes (e.g., sodium chloride, potassium chloride, calcium chloride, sodium lactate, sodium dihydrogenphosphate, sodium carbonate, magnesium carbonate), saccharides (e.g., glucose, fructose, sorbitol, mannitol, dextran), protein amino acids (e.g., glycine, aspartic acid, lysine) and vitamins (e.g., vitamin B1, vitamin C).

The agent comprising (2R)-2-propyloctanoic acid or a salt thereof to be used in the method of the present invention is useful for the treatment of neurodegenerative diseases. In this case, the neurodegenerative diseases include all diseases which are accompanied by degeneration of nerve cells and are not limited by the cause of diseases. The nerve cells may be any type of nerve cells in vivo and, for example, they may be cells of central nerves (e.g., cranial nerves, spinal nerves) or peripheral nerves (e.g., of autonomic nerve system (such as sympathetic nerve and parasympathetic nerve)) and the like. The neurodegenerative diseases are desirably diseases of central nerves, and their examples include Alzheimer disease, amyotrophic lateral sclerosis, progressive supranuclear palsy, olivopontocerebellar atrophy, strokes (e.g., cerebral bleeding (such as hypertensive intracerebral hemorrhage), cerebral infarction (such as cerebral thrombosis and cerebral embolism), transient ischemic attack, subarachnoid hemorrhage), neurological dysfunction after brain injury, demyelinating diseases (e.g., multiple sclerosis), brain tumors (e.g., astrocytoma), infectious diseases (e.g., meningitis, brain abscess, Creutzfeldt-Jacob disease, AIDS dementia), Parkinson disease and the like. More preferred as the neurodegenerative diseases are, for example, stroke and the like, and particularly preferred are, for example, cerebral infarction and the like. Acute phase cerebral infarction is most particularly desirable. Though it should not be interpreted strictly, the acute phase cerebral infarction means cerebral infarction within 2 weeks after onset.

The agent comprising (2R)-2-propyloctanoic acid or a salt thereof, to be used in the method of the present invention, is also useful for the treatment of a disease whose treatment requires neural regeneration. In this case, the neural regeneration includes both of "neural neogenesis" and "neural regeneration" as the terms used in said field. Also, the neural regeneration means that the process of normal development in nerve cells is at least partially reproduced, and it is not influenced by the origin of the cells to be regenerated. Examples of the cells to be regenerated include stem cells (e.g., nervous stem cell, embryonic stem cell, bone marrow cell), nerve precursor cells, nerve cells and the like. In addition, the nerve cells to be regenerated may be either endogenous cells (e.g., nerve stem cell, nerve precursor cell, nerve cell, mature nerve cell) or exogenous cells (e.g., grafted nerve stem cell, grafted nerve precursor cell, grafted nerve cell, grafted mature nerve cell). The exogenous cells may be either autogenous cells or heterogeneous cells. In addition, even in the case of cells less differentiated than nerve stem cells, all of those which are to differentiate into nerve stem cells are included in the neural regeneration according to the present invention. Also, the neural regeneration includes tissue regeneration or functional regeneration, and, for example, survival, differentiation, proliferation and/or maturation of the above cells are included. The term maturation as used herein means, for example, that a nerve cell grows into a proper state to fulfill functions such as exchange of signals. In addition, the regeneration also includes neurotrophic factor-like action and neurotrophic factor activity-reinforcing action. The term neurotrophic factor as used herein means a factor which acts as a nutrient of, for example, nerve stem cell, nerve precursor cell, nerve cell, mature nerve cell and the like. Examples of the neurotrophic factor-like action include axon elongation action, neurotransmitter synthesis accelerating action, action to accelerate differentiation and proliferation of nerve cells and action as a nutrition for maintaining the activity of nerve cells, though not limited thereto. In addition, the neurotrophic factor activity reinforcing action means the activity to reinforce actions of the above neurotrophic factor.

The agent to be used in the method of the present invention, comprising (2R)-2-propyloctanoic acid or a salt thereof is also useful in treating neuropathy. The term "neuropathy" as used herein includes all neurological dysfunctions. Examples of the neuropathy include transient blindness (e.g., transient amaurosis), disturbance of consciousness, hemiplegia, sensory disturbance, homonymous hemianopsia, aphasia, alternate hemiplegia, two-side quadriplegia, vertigo, ear noises, nystagmus, double vision, coma and the like, and preferred are these neuropathies accompanied by neurodegenerative diseases. Although the type of the neuropathy accompanying a neurodegenerative disease, such as the neuropathy in cerebral infarction, varies depending on the region of blood vessel obstruction and its symptoms also vary depending on the degree of the disorder, the above neuropathies are mainly observed. In addition, the presence or absence of neuropathy in cerebral infarction may be judged by various diagnosing tests known in this technical field for the detection of neuropathy. Illustrative examples of said diagnosing tests include Glasgow Outcome Scale (GOS), Glasgow Coma Scale (GCS), Rankin Scale (RS), modified Rankin Scale (mRS), Disability Rating Scale (DRS), NIH Stroke Scale (NIH SS) and the like, and these can be carried out using known methods. These neuropathy-detecting diagnosing tests may be carried out by optionally combining with a physical testing method for detecting abnormality in the brain, such as CAT-scan, intracranial pressure measurement or the like. In general, in the clinical tests on patients with cerebral infarction as the subjects, the effectiveness is evaluated by carrying out the above diagnosing tests as the main evaluation item. In addition, if necessary, conventionally known evaluation items such as level of consciousness, motor function, Barthel Index, general safety, outcome, head CT findings, head MRI findings, blood pressure, pulse, body temperature and general clinical tests may be evaluated as secondary evaluation items by conventionally known methods and used in the evaluation of effectiveness, alone or in combination with the main evaluation item.

The agent comprising (2R)-2-propyloctanoic acid or a salt thereof to be used in the method of the present invention has an inhibitory activity against S-100β increase. By inhibition of S-100β increase, the (2R)-2-propyloctanoic acid or a salt thereof can also function as a therapeutic agent of the above disorders and diseases (e.g., a neurodegenerative disease, a neuropathy or a disease whose treatment requires neural regeneration). The inhibitory action against S-100β increase of (2R)-2-propyloctanoic acid or a salt thereof does not limit its acting region to the brain tissues. That is, it may be either a systemic action or a local action, or the S-100β increase inhibiting action may be observed systemically or topically. The S-100β detection method for use in the verification of the S-100β increase inhibiting action is not particularly limited, so long as it is a method which can detect S-100β. Regarding the S-100β detection method, it can be measured in biological samples, such as a blood sample of a patient or a fraction thereof (e.g., serum) and cerebrospinal fluid, by using a commercially available kit released, for example, from Byc-Sangtec Diagnostica GmbH & Co. (Diezenbach, Germany) or Syn-X Pharma, Inc. (Ontario, Canada), such as a radioimmunoassay kit, a luminescence immunoassay kit, a fluorescence immunoassay kit or a calorimetric immunoassay kit. Also, depending on the number of samples to be tested, it may be measured using the known methods employed by those skilled in the art for the detection of protein, such as various biological test methods which use an anti-S-100β antibody (e.g., western blotting, immunoprecipitation, and flow cytometry). Regarding the inhibitory action against S-100β increase by (2R)-2-propyloctanoic acid or a salt thereof, the activity detected in a blood sample of a patient or a fraction thereof (e.g., serum) is preferred. The inhibitory action against S-100β increase in a blood sample of a patient or a fraction thereof (e.g., serum) is not influenced by the cause of the increase of S-100β or the action mechanism of S-100β increase inhibition. For example, increase in the S-100β in a blood sample of a patient or a fraction thereof (e.g., serum) may reflect its increase caused by a damage on topical infarction foci or its peripheral brain tissue or on the whole brain tissue, or may reflect that the S-100β at a level generally existing in the cells is released due to disorders in tissues or cells. Also, the inhibitory action against S-100β increase in a blood sample of a patient or a fraction thereof (e.g., serum) may be caused either by the inhibition of expansion of infarction foci, by the inhibition of S-100β outflow from a brain tissue into blood, or by the inhibition of increase in S-100β at a cellular level.

Regarding the method of the present invention for administering (2R)-2-propyloctanoic acid or a salt thereof to a patient for the treatment of a neurodegenerative disease, a neuropathy or a disease whose treatment requires neural regeneration, this method is not particularly limited, so long as it is a method which parenterally administers it in an amount of about 100 mg or more (e.g., from about 100 mg to about 2,000 mg) per dose, but the followings can be exemplified as illustrative administration period, administration frequency, dose and administration method for obtaining desirable therapeutic effects on the above diseases.

Regarding the administration period, in order to obtain desirable therapeutic effects on the above diseases, the agent may be administered continuously for an optional number of days. Also, if necessary, it may be intermittently administered by setting appropriate drug cessation periods. As the illustrative administration period, a period for 1 to 100 days can be exemplified. The preferred administration period is for example from 1 to 10 days, more preferred administration period is for example 3 days, 4 days, 5 days, 6 days or 7 days, and most preferred administration period is for example 7 days.

Regarding the administration frequency, in order to obtain desirable therapeutic effects on the above diseases, the agent may be administered at an optional frequency. In addition, it may be changed depending on the condition of each patient and other reasons. As the illustrative administration frequency per day, from 1 to 5 times per day can be exemplified. Preferred administration frequency per day is, for example, from 1 to 3 times, more preferred administration frequency per day is, for example, 1 or 2 times, and most preferred administration frequency per day is, for example, once a day.

The dosage amount is not particularly limited, so long as it is about 100 mg or more (e.g., from about 100 mg to about 2,000 mg) per one dose as described in the foregoing, but in order to obtain desirable therapeutic effects on the above diseases, it is preferable to determine the amount depending on the body weight of each patient. In the case of the parenteral administration of (2R)-2-propyloctanoic acid, it is desirable to administer for example from about 2 mg to about 12 mg per 1 kg of body weight of each patient. As the more specific example of the amount, about 2 mg, about 4 mg, about 6 mg, about 8 mg, about 10 mg or about 12 mg per 1 kg of body weight of each patient can be cited. As more preferred amount, about 4 mg, about 6 mg, about 8 mg or about 10 mg per 1 kg of body weight of each patient can be cited, and as the most preferred amount, about 4 mg or about 8 mg per 1 kg of body weight of each patient can be cited. In addition, when a salt of (2R)-2-propyloctanoic acid is parenterally administered, the above amounts described as the amount of (2R)-2-propyloctanoic acid is suitably applied.

The administration method is not particularly limited, so long as it is a parenteral administration method as described in the foregoing, but in order to obtain desirable therapeutic effects on the above diseases, it is desirable to use the agent by preparing it into dosage forms which can be intravenously administered, such as injections and infusions. Administration of (2R)-2-propyloctanoic acid or a salt thereof in a dosage form which can be intravenously administered enables quick expression of the effect. In addition, preparation of (2R)-2-propyloctanoic acid or a salt thereof into such dosage forms which can be intravenously administered can avoid side effects accompanying sudden increase in its blood level and, if necessary, can even control of the blood level and the like, for example by carrying out its continuous intravenous administration using a syringe, infusion bag or the like. The period of continuous administration is not particularly limited and may be changed depending on the condition of each patient or other reasons, but it is desirable to carry out the continuous administration, for example, over an about 0.5 to about 3 hour period of time, preferably about 0.5 to about 1.5 hours, particularly preferably about 1 hour.

Regarding a desirable method according to the present invention for parenterally administering from about 100 mg to about 2,000 mg per dose of (2R)-2-propyloctanoic acid or a salt thereof for the treatment of a neurodegenerative disease, a neuropathy or a disease whose treatment requires neural regeneration, its examples include a method in which (2R)-2-propyloctanoic acid or a salt thereof is continuously administered into a vein spending about 1 hour once a day using an infusion bag or the like, at a dose of about 2 mg to about 12 mg per 1 kg of body weight of each patient during a drug administration period of 1 day to 100 days.

The agent to be used in the method of the present invention which comprises (2R)-2-propyloctanoic acid or a salt thereof may be jointly used with other agents such as antiepileptic agents (e.g., phenobarbital, mephobarbital, metharbital, primidone, phenytoin, ethotoin, trimethadione, ethosuximide, acetyl pheneturide, carbamazepine, acetazolamide, diazepam, sodium valproate), acetylcholine esterase inhibitors (e.g., donepezil hydrochloride, TAK-147, rivastigmine, galantamin), neurotrophic factors (e.g., ABS-205), aldose reductase inhibitors, anti-thrombus agents (e.g., t-PA, heparin), oral anticoagulant (e.g., warfarin), synthetic anti-thrombin agents (e.g., gabexate mesylate, nafamostat mesylate, argatroban), anti-platelet agents (e.g., aspirin, dipyridamole, ticlopidine hydrochloride, beraprost sodium, cilostazol, ozagrel sodium), thrombolytic agents (urokinase, tisokinase, alteplase), factor Xa inhibitors, factor VIIa inhibitors, cerebral circulation metabolism improving agents (e.g., idebenone, calcium hopantenate, amantadine hydrochloride, meclofenoxate hydrochloride, dihydroergotoxin mesylate, pyrithioxine hydrochloride, γ-aminobutyric acid, bifemelane hydrochloride, lisuride maleate, indeloxazine hydrochloride, nicergoline, propentofylline), antioxidants (e.g., edaravone), glycerin preparations (e.g., glyceol), β-secretase inhibitors (e.g., 6-(4-biphenylyl)methoxy-2-[2-(N,N-dimethylamino) ethyl]tetralin, 6-(4-biphenylyl)methoxy-2-(N,N-dimethylamino)methyltetralin, 6-(4-biphenylyl)methoxy-2-(N,N-dipropylamino)methyltetralin, 2-(N,N-dimethylamino) methyl-6-(4'-methoxybiphenyl-4-yl)methoxytetralin, 6-(4-biphenylyl)methoxy-2-[2-(N,N-diethylamino)ethyl]tetralin, 2-[2-(N,N-dimethylamino)ethyl]-6-(4'-methylbiphenyl-4-yl)methoxytetralin, 2-[2-(N,N-dimethylamino)ethyl]-6-(4'-methoxybiphenyl-4-yl)methoxytetralin, 6-(2',4'-dimethoxybiphenyl-4-yl)methoxy-2-[2-(N,N-dimethylamino)ethyl] tetralin, 6-[4-(1,3-benzodioxol-5-yl)phenyl]methoxy-2-[2-(N,N-dimethylamino)ethyl]tetralin, 6-(3',4'-dimethoxybiphenyl-4-yl)methoxy-2-[2-(N,N-dimethylamino)ethyl]tetralin, optically active substances thereof, salts thereof and hydrates thereof, OM99-2 (WO 01/00663)), β-amyloid protein aggregation inhibitors (e.g., PTI-00703, ALZHEMED (NC-531), PPI-368 (JP-A-11-514333), PPI-558 (JP-A-2001-500852), SKF-74652 (Biochem. J., 340 (1), 283-289 (1999))), brain function activators (e.g., aniracetam, nicergoline), dopamine receptor agonists (e.g., L-dopa, bromocriptine, pergolide, talipexole, pramipexole, cabergoline, amantadine), monoamine oxidase (MAO) inhibitors (e.g., safrazine, deprenyl, selgiline (selegiline), remacemide, riluzole), anticholinergic agents (e.g., trihexyphenidyl, biperidene), COMT inhibitors (e.g., entakapon), amyotrophic lateral sclerosis treating agents (e.g., riluzole, neurotrophic factors), statin-based hyperlipemia treating agents (e.g., pravastatin sodium, atrovastatin, simvastatin, rosvastatin), fibrate-based hyperlipemia treating agents (e.g., clofibrate), apoptosis inhibitors (e.g., CPI-1189, IDN-6556, CEP-1347), nerve differentiation/regeneration accelerators (e.g., leteprinim, xaliproden (SR-57746-A), SB-216763), non-steroidal anti-inflammatory agents (e.g., meloxicam, tenoxicam, indomethacin, ibuprofen, celecoxib, rofecoxib, aspirin), steroid agents (e.g., dexamethasone, hexoestrol, cortisone acetate), sex hormones or derivatives thereof (e.g., progesterone, estradiol, estradiol benzoate) and the like. In addition, it may also be used jointly with a nicotine receptor modulating agent, a γ-secretase inhibitor, a β-amyloid vaccine, a β-amyloid hydrolase, a squalene synthase inhibitor, an agent for treating abnormal behavior, wandering and the like accompanied by the advance of dementia, an anti-hypertensive agent, a diabetes treating agent, an antidepressant, an anti-anxiety agent, a disease-modifying anti-rheumatic drug, an anti-cytokine agent (e.g., TNF inhibitor, MAP kinase inhibitor), parathyroid hormone (PTH), a calcium receptor antagonist and the like. The above joint use agents are merely examples and not limited thereto. These other agents may be administered by an optional combination of two or more. In addition, not only the compounds so far discovered but also those which will be found in the future are included in the agents to be jointly used.

Among the above neurodegenerative diseases, neuropathies and diseases whose treatment involve neural regeneration, for example, when diseases with formation of blood clot such as cerebral infarction are treated, an agent comprising (2R)-2-propyloctanoic acid or a salt thereof is preferably administered in combination with t-PA among other drugs exemplified as above. When they are used in combination, excellent therapy effect can be obtained in comparison with the case where each of the agents is used alone. The method of administrating a combination of the agent comprising (2R)-2-propyloctanoic acid or a salt thereof with t-PA is not limited in particular, but preferably, they are administered in combination according to a dosage and an administration method employed when each of the agents is used alone. The independent dosage and administration method of the agent comprising (2R)-2-propyloctanoic acid or a salt thereof are described above. In addition, the independent dosage and administration method of t-PA include a method in which about 0.6 mg or about 0.9 mg of t-PA per 1 kg of body weight of the patient is parenterally, preferably intravenously, administered within 6 hours, preferably 3 hours, after onset of cerebral infarction. More specifically, 10% of the total amount to be administered is administered rapidly in a few minutes (e.g., about 1 minute to about 2 minutes), and the residual is administered continuously over about 1 hour. Accordingly, if the agent comprising (2R)-2-propyloctanoic acid or a salt thereof and t-PA are used in combination, for example, t-PA is administered within 3 hours after onset of cerebral infarction according to the above method, and the agent comprising (2R)-2-propyloctanoic acid or a salt thereof is administered at any time, preferably within 2 weeks after onset of cerebral infarction, and more preferably within 72 hours after onset of cerebral infarction, in accordance with the above administration period, administration frequency, dosage and administration method of (2R)-2-propyloctanoic acid. Consequently, t-PA and (2R)-2-propyloctanoic acid or a salt thereof can be administered at the same time within 3 hours after onset of cerebral infarction. When they are administered at the same time, separate formulations may be used, or a single formulation which contains t-PA and (2R)-2-propyloctanoic acid or a salt thereof in it may be used. Of course, these injection methods are illustrations, and the dose may be increased and decreased depending on the condition of the patient appropriately.

[Toxicity]

As is shown in the following examples, (2R)-2-propyloctanoic acid or a salt thereof has markedly low toxicity and can be judged sufficiently safe so far as it is used in mammals, particularly humans, by the method and dosage of the present invention.

EFFECTS OF THE INVENTION

The agent of the present invention for parenteral administration for preventing and/or treating a neurodegenerative disease, a neuropathy or a disease whose treatment requires neural regeneration, comprising (2R)-2-propyloctanoic acid or a salt thereof, is safe and can markedly improve these diseases, particularly various symptoms accompanying neurodegenerative diseases such as cerebral infarction. In addition to this, the compound is markedly useful as a medicament, because it shows the effect in the case of cerebral infarction 3 hours or more after the onset of the disease, which is difficult to treat by the conventional therapeutic agents. Additionally, more excellent therapeutic effect can be obtained by administering the agent comprising (2R)-2-propyloctanoic acid or a salt thereof to patients who have been treated with t-PA in a hospital within 3 hours after onset of cerebral infarction in comparison with the treatment with t-PA alone.

[Application to Medicament]

The agent of the present invention for parenteral administration for preventing and/or treating a neurodegenerative disease, a neuropathy or a disease whose treatment requires neural regeneration, comprising (2R)-2-propyloctanoic acid or a salt thereof, can be used in mammals (e.g., human and non-human animals such as monkey, sheep, cattle, horse, dog, cat, rabbit, rat and mouse) and the like. Particularly, desirable therapeutic effects upon neurodegenerative diseases, neuropathies or diseases whose treatment require neural regeneration can be obtained by parenterally administering it to mammals, particularly human, by the administration method and dosage of the present invention. The method and dose of the present invention are suitable for obtaining improving effects of various symptoms of cerebral infarction patients. In the present invention, the administration may be started at any time after onset of cerebral infarction. It is desirable to carry out the administration preferably within 2 weeks, more preferably within 2 to 5 days, most preferably within 24 hours, and particularly preferably within 6 hours namely TTW of cerebral infarction. The method of the present invention overcame the limitation on the administration period of therapeutic agents such as t-PA used in the conventional cerebral infarction treatment, so that the effects obtained by said method are markedly excellent.

BEST MODE FOR CARRYING OUT THE INVENTION

Clinical effects of (2R)-2-propyloctanoic acid or a salt thereof for patients with cerebral infarction using the administration method and dosage of the present invention are described below in detail with reference to the inventive and formulation examples, although the present invention is not limited thereto. In addition, the contents may be changed within the range not departing the scope of the present invention.

Example 1

As a clinical test, a randomization test was carried out on patients with cerebral infarction at the acute phase (within 72 hours after onset of the disease), at two doses under the following conditions.

Object: 97 patients in the acute phase cerebral infarction.
Administration method and dosage: 1 hour of continuous intravenous administration once a day in each group;
(1) (2R)-2-propyloctanoic acid: 0.4 mg/kg/h;
(2) (2R)-2-propyloctanoic acid: 4 mg/kg/h.
Administration period: 7 days
The Number of Cases:
(1) (2R)-2-propyloctanoic acid 0.4 mg/kg/h administered group: 51 patients;
(2) (2R)-2-propyloctanoic acid 4 mg/kg/h administered group: 46 patients.
Evaluation Items:
Main Evaluation Items
<Efficacy Evaluation Items>
(1) Rankin Scale (RS)
Evaluation method: Symptoms of patients were scored by classifying them into the following grades of Table 1.

TABLE 1

| 0 | No disorders | All daily activities are possible. |
|---|---|---|
| 1 | Very slight | Activities which were formerly possible are partially limited. |
| 2 | Slight | Active walking is possible, but slight assistance is necessary for personal activities. |
| 3 | Moderate | Slight assistance is necessary for walking and personal activities. |
| 4 | Moderately severe | Assistance is necessary for walking and personal activities. |
| 5 | Severe | Life on a bed, assistance and observation are always required. |

(2) Glasgow Outcome Scale (GOS)
Evaluation method: Symptoms of patients were scored by classifying them into the following grades of Table 2.

TABLE 2

| 1 | Good recovery | Can make usual personal life independent of the presence of minimum neurological disorders. |
|---|---|---|
| 2 | Moderate disability | Has neurological or intellectual personality disorders, but can make life without assistance. |
| 3 | Severe disability | Has consciousness, but totally requires assistance from others for making daily life. |
| 4 | Continuation of vegetative state | |
| 5 | Dead | |

Figure 1:
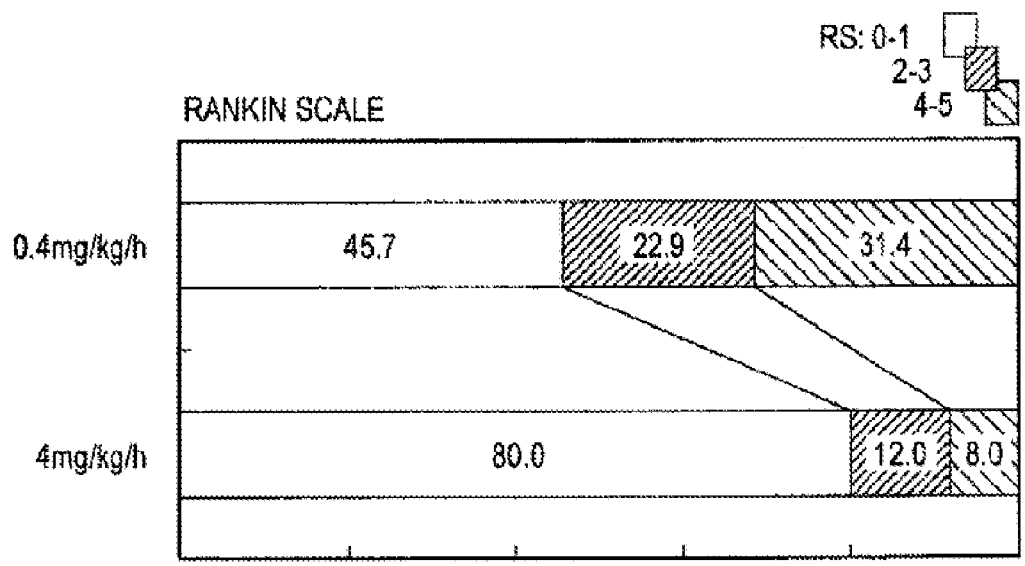
FIG. 1 shows a result of the analysis of clinical data obtained in Clinical Test Example 1 in accordance with the efficacy evaluation item (Rankin Scale) described in Clinical Test Example 1.
Figure 2:
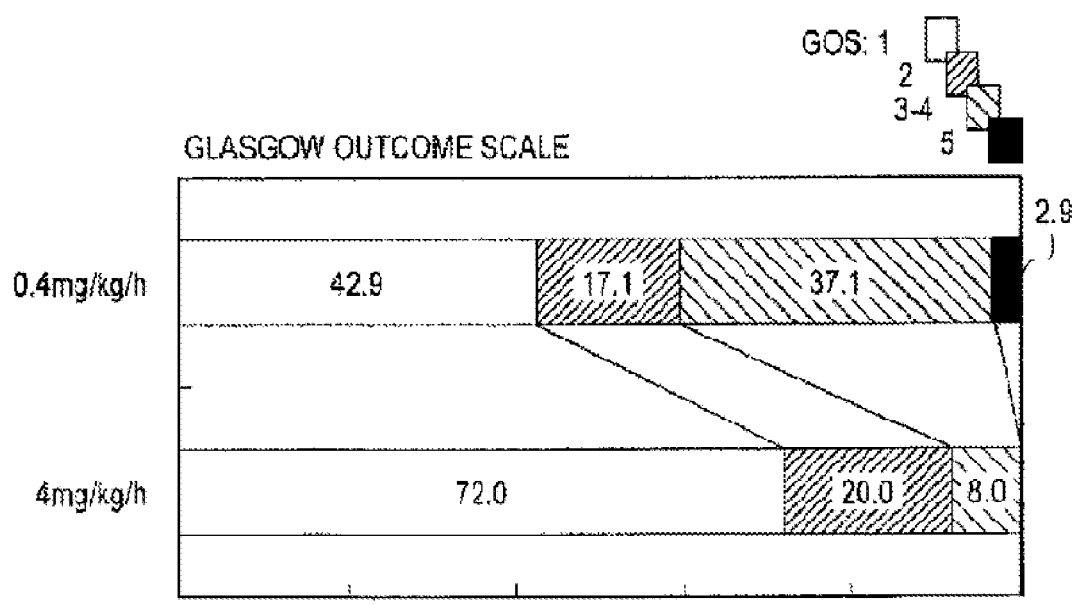
FIG. 2 shows a result of the analysis of clinical data obtained in Clinical Test Example 1 in accordance with the efficacy evaluation item (Glasgow Outcome Scale) described in Clinical Test Example 1.

<Safety Evaluation Item>
Frequency of adverse matters and the contents thereof (symptoms, causal relation and the like):
Analysis: Therapeutic effects by continuous intravenous administration of (2R)-2-propyloctanoic acid were evaluated based on the above main evaluation items.
Results: The results are shown below.
<Efficacy Evaluation Item>
In cases of the disease wherein the Japan Stroke Scale (JSS: evaluated in accordance with a reference (Stroke, 32, 1800-1807 (2001)) before the administration was 15 or less (JSS≦15), statistically significant differences were found between the 0.4 mg/kg/h administration group and the 4 mg/kg/h administration group, in terms of the ratio of occupying the category of improvement by RS and GOS three months after the commencement of administration. The results are shown in FIG. 1 and FIG. 2.
<Safety Evaluation Item>
Seven cases of death (3 cases in the 0.4 mg/kg/h administration group and 4 cases in the 4 mg/kg/h administration group) were found in this test, and one case of other serious adverse matter in the 0.4 mg/kg/h administration group, but their causal relation to the test drug was denied. Frequency of the adverse matters was 78.9% in the 0.4 mg/kg/h administration group and 74.1% in the 4 mg/kg/h administration group, showing no significant difference between both groups. Frequency of side effects was 43.9% in the 0.4 mg/kg/h administration group and 44.4% in the 4 mg/kg/h administration group, showing no significant difference between both groups. The main content of the side effects was increase in the liver function parameters "AST (GOT), ALT (GPT), γ-GTP, A1-p, LDH and total bilirubin", but they were not serious.

Example 2

As a clinical test, a double blind test was carried out using patients with cerebral infarction at the acute phase (within 24 hours after onset of the disease) under the following conditions by (2R)-2-propyloctanoic acid administration groups (6 varied doses) and a placebo administration group.
Object: 92 patients in the acute phase cerebral infarction.
Administration method and dosage: 1 hour of continuous intravenous administration once a day in each group;
(1) (2R)-2-propyloctanoic acid: 2 mg/kg/h;
(2) (2R)-2-propyloctanoic acid: 4 mg/kg/h;
(3) (2R)-2-propyloctanoic acid: 6 mg/kg/h;
(4) (2R)-2-propyloctanoic acid: 8 mg/kg/h;
(5) (2R)-2-propyloctanoic acid: 10 mg/kg/h;
(6) (2R)-2-propyloctanoic acid: 12 mg/kg/h;
(7) placebo.
Administration period: 7 days
The Number of Cases:
(1) (2R)-2-propyloctanoic acid 2 mg/kg/h administered group: 9 patients;
(2) (2R)-2-propyloctanoic acid 4 mg/kg/h administered group: 8 patients;
(3) (2R)-2-propyloctanoic acid 6 mg/kg/h administered group: 8 patients;
(4) (2R)-2-propyloctanoic acid 8 mg/kg/h administered group: 8 patients;
(5) (2R)-2-propyloctanoic acid 10 mg/kg/h administered group: 8 patients;
(6) (2R)-2-propyloctanoic acid 12 mg/kg/h administered group: 8 patients;
(7) placebo administered group: 43 patients.
Evaluation Items:
Main Evaluation Items
<Efficacy Evaluation Items>
(1) Modified Rankin Scale (mRS)
Evaluation method: Symptoms of patients were scored by classifying them into the following grades of Table 3.

TABLE 3

| 0 | No symptoms at all. |
|---|---|
| 1 | No significant disability despite symptoms: able to carry out all usual duties and activities. |
| 2 | Slight disability: unable to carry out all previous activities, but able to look after own affairs without assistance. |
| 3 | Moderate disability: requiring some assistance, but able to walk without assistance. |
| 4 | Moderately severe disability: unable to walk without assistance and unable to attend to own bodily needs without assistance. |
| 5 | Severe disability: bedridden, incontinent and requiring constant nursing care and attention. |
| 6 | Dead. |

(2) The Serum S-100β Content

Evaluation method: Blood samples were collected from patients and evaluated in accordance with the following methods.

(2-1) Collection of Blood Samples

The blood samples for use in the S-100β measurement were collected before the administration on the 1st to 7th days (pre-infusion) and after 3 hours, 7 hours, 12 hours and 24 hours of the administration on the 1st, 3rd and 7th days (post-infusion). In this case, the same blood samples collected after 24 hours of administration on the 1st and 3rd days were respectively used as the blood samples before administration on the 2nd and 4th days.

A blood sample (3 ml) was collected from each patient using a catheter or by venipuncture. Each sample was coagulated for 30 minutes and then centrifuged at 3,500 rpm for 12 to 15 minutes. Serum was recovered and dispensed in about 0.5 ml portions into two containers. The serum samples were labeled and stored at −20° C. until the S-100β assay.

(2-2) S-100β Assay

The SMART S100 ELISA Kit (Syn-X Pharma, Inc. (Ontario, Canada) having a measuring range of 0.02 to 1.6 ng/ml was used for the S-100β assay.

<Safety Evaluation Item>

Adverse Matters and Clinical Test Values

Analysis: Therapeutic effects by continuous intravenous administration of (2R)-2-propyloctanoic acid was evaluated based on the above main evaluation items.

Results: The results are shown below.

<Efficacy Evaluation Item>

As a result of evaluating modified Rankin Scale (mRS) 40 days after the commencement of administration, a statistically significant difference was found between the placebo administration group and the 8 mg/kg/h (2R)-2-propyloctanoic acid administration group (placebo administration group: 32.5%, 8 mg/kg/h (2R)-2-propyloctanoic acid administration group: 87.5%), in terms of the ratio occupied by a score of 2 or less which corresponds to the category of good improvement.

Figure 3:
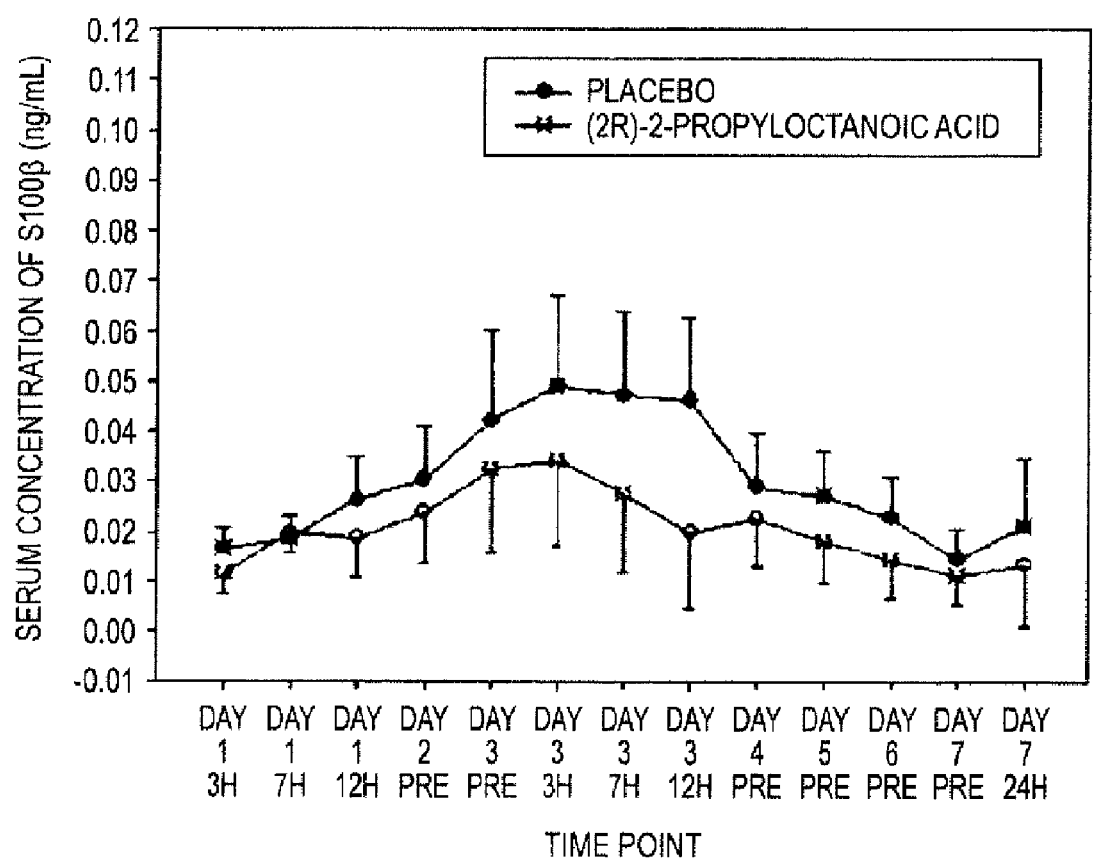
FIG. 3 shows a result of the analysis of clinical data obtained in Clinical Test Example 2 in accordance with the efficacy evaluation item (serum S-100β content) described in Clinical Test Example 2.

Also, as a result of evaluating the serum S-100β content during the administration period, a tendency of inhibiting increase of the serum S-100β content after onset of cerebral infarction was observed in the (2R)-2-propyloctanoic acid administered groups in comparison with the placebo group. This tendency was particularly remarkable on and after 3 days of the commencement of administration. The results are shown in FIG. 3.

<Safety Evaluation Item>

Serious adverse matters were found in 10 cases in the (2R)-2-propyloctanoic acid administration group and 12 cases in the placebo administration group, but their causal relation to the test drug was denied. Frequency of the adverse matters was 98% in the (2R)-2-propyloctanoic acid administration group and 100% in the placebo administration group, showing no difference between both groups. Frequency of the adverse matters (side effects) whose causal relation to the test drug was not denied was 42.9% in the (2R)-2-propyloctanoic acid administration group and 39.5% in the placebo administration group, showing no difference between both groups.

In addition, a side effect of increasing the dose-dependent expression frequency was not found, too.

Formulation Examples

Production of (2R)-2-propyloctanoic acid-containing Injections

Formulation Example 1

| | |
|---|---|
| (2R)-2-Propyloctanoic acid | 2.0 kg |
| Sodium phosphate•12H$_2$O | 3.54 kg |

Each of the above components was added to distilled water for injection, and the volume was adjusted to 40 liters using distilled water for injection. This was made into a uniform solution, filtered through a sterile filter (Durapore 0.22 μm membrane), dispensed in 2 ml portions into plastic ampoules and then subjected to high pressure steam sterilization (123° C., 15 minutes), thereby obtaining 20,000 ampoules containing 100 mg of the active ingredients per one ampoule.

INDUSTRIAL APPLICABILITY

The parenteral administration therapeutic agent of the present invention for a neurodegenerative disease, a neuropathy or a disease whose treatment requires neural regeneration, comprising (2R)-2-propyloctanoic acid or a salt thereof, is safe and can markedly improve these diseases, particularly various symptoms accompanied by neurodegenerative diseases such as cerebral infarction. In addition to this, the compound is markedly useful as a medicament, because it shows the effect in the case of cerebral infarction in 3 hours or more after the onset of the disease, which is difficult to treat by the conventional therapeutic agents.

The invention claimed is:

1. A method of treating cerebral infarction, comprising parenterally administering to a human between about 100 mg to about 2,000 mg of (2R)-2-propyloctanoic acid or a salt thereof for about 0.5 to about 3 hours once a day for a period of treatment lasting from 1 to 100 days.

2. The method according to claim 1, wherein the parenteral administration is intravenous administration.

3. The method according to claim 2, wherein the intravenous administration is continuous administration.

4. The method according to claim 3, wherein the continuous administration is infusion bag administration.

5. The method according to claim 1, wherein the administration period is from 1 day to 10 days.

6. The method according to claim 5, wherein the administration period is 3 days, 4 days, 5 days, 6 days or 7 days.

7. The method according to claim 6, wherein the administration period is 7 days.

8. The method according to claim 1, wherein the dose per 1 kg of body weight of a patient is within a range of about 2 mg to about 12 mg.

9. The method according to claim 8, wherein the dose per 1 kg of body weight of a patient is about 2 mg, about 4 mg, about 6 mg, about 8 mg, about 10 mg or about 12 mg.

10. The method according to claim 9, wherein the dose per 1 kg of body weight of a patient is about 4 mg or about 8 mg.

11. The method according to claim 1, which is a method for inhibition of S-100β increase.

12. The method according to claim 1, wherein (2R)-2-propyloctanoic acid is used.

13. A method for treating cerebral infarction, comprising continuously administering (2R)-2-propyloctanoic acid intravenously to a human using an infusion bag at a dose of about 4 mg or about 8 mg per 1 kg of body weight for about 1 hour once a day during an administration period of 7 days.

14. The method according to claim 1, wherein the period of time is 1 hour.

* * * * *